United States Patent [19]

Lovelace

[11] 3,932,544

[45] Jan. 13, 1976

[54] PROCESS FOR PRODUCTION OF MESO-1,2,3,4-TETRACHLOROBUTANE

[75] Inventor: Billy J. Lovelace, Baytown, Tex.

[73] Assignee: Petro-Tex Chemical Corporation, Houston, Tex.

[22] Filed: July 1, 1974

[21] Appl. No.: 484,944

[52] U.S. Cl.............................................. 260/658 R
[51] Int. Cl.² ........................................ C07C 17/04
[58] Field of Search ................... 260/658 R, 660

[56] References Cited
UNITED STATES PATENTS

| | | | |
|---|---|---|---|
| 2,350,373 | 6/1944 | Soday | 260/660 |
| 2,374,711 | 5/1945 | Soday | 260/660 |
| 2,445,729 | 7/1948 | Radcliffe et al. | 260/660 |

FOREIGN PATENTS OR APPLICATIONS

| | | | |
|---|---|---|---|
| 38,802 | 12/1970 | Japan | 260/658 R |
| 1,019,131 | 2/1966 | United Kingdom | 260/660 |
| 1,019,149 | 2/1966 | United Kingdom | 260/660 |

*Primary Examiner*—D. Horwitz
*Assistant Examiner*—Joseph A. Boska
*Attorney, Agent, or Firm*—N. Elton Dry; Kenneth H. Johnson

[57] ABSTRACT

Meso-1,2,3,4-tetrachlorobutane is produced in an improved liquid phase chlorination process wherein trans-1,4-dichlorobutene-2 is contacted with chlorine which is added to the reaction zone throughout the chlorination reaction at a rate of from about 0.01 to about 2.0 mole percent per minute based on the amount of trans-1,4-dichlorobutene-2 initially present.

11 Claims, No Drawings

PROCESS FOR PRODUCTION OF MESO-1,2,3,4-TETRACHLOROBUTANE

BACKGROUND OF THE INVENTION

1. Field of the Invention.

The present invention relates to the production of meso-1,2,3,4-tetrachlorobutane, which compound is of established utility in the production of 2,3-dichlorobutadiene. More particularly, this invention relates to a method for preparing meso-1,2,3,4-tetrachlorobutane from trans-1,4-dichlorobutene-2 in a liquid phase chlorination process.

2. Description of the Prior Art.

In preparing meso-1,2,3,4-tetrachlorobutane from dichlorobutenes in a liquid phase chlorination process, there are produced, in addition to the desired meso-isomer, the dextrorotatory and levorotatory 1,2,3,4-tetrachlorobutanes (the racemic mixture is referred to as dl-isomer) and a proportion of chlorinated materials designated as heavy ends. These heavy ends are generally more highly chlorinated products such as the pentachlorobutanes. The formation of dl-isomer and heavy ends is undesirable in that these materials represent a yield loss and are undesirable contaminants in the desired meso-1,2,3,4-tetrachlorobutane product.

Known methods for preparing meso-1,2,3,4-tetrachlorobutane from dichlorobutenes in a liquid phase chlorination process have been generally unsatisfactory. Noncatalytic processes, such as those disclosed in Japanese Pat. No. 38,802 (1970) and in the Journal of the American Chemical Society 73, 244–6 (1951), require extremely low temperatures of from 0°C. to about −30°C. and are, therefore, generally undesirable economically. Known processes for carrying out the chlorination reaction at moderate temperatures in the range of from about 50°C.–150°C. involve the use of a catalyst. See, for example, the process disclosed in French Pat. No. 1,401,077 (titanium tetrachloride catalysts), French Pat. No. 1,401,078 (pyridine catalysts), and U.S. Pat. No. 2,445,729 (ferric chloride or antimony pentachloride catalysts). All of these processes are generally unsatisfactory in that there are produced a large proportion of heavy ends material and an undesirably large proportion of the dl-isomer. These catalytic processes are additionally undesirable due to the presence of the metallic catalyst in the reaction product.

SUMMARY OF THE INVENTION

According to the improved process of the instant invention, meso-1,2,3,4-tetrachlorobutane is produced by contacting trans-1,4-dichlorobutene-2 with a chlorine-containing gas in a non-catalytic liquid phase chlorination wherein the chlorine-containing gas is added to the reaction zone at a rate of from about 0.01 to about 2.0 mole percent per minute based on the amount of dichlorobutenes initially present.

DESCRIPTION OF THE PREFERRED EMBODIMENTS

In accordance with the process of this invention, meso-1,2,3,4-tetrachlorobutane is produced in high yield by the chlorination of certain dichlorobutenes under conditions in which the rate at which the chlorine is introduced into the reaction zone is maintained at relatively low levels. Effecting the chlorination of the trans-1,4-dichlorobutene-2 at such relatively low chlorination rates has been found to enhance the formation of the meso-isomer and to suppress the formation of more highly chlorinated derivatives of the dichlorobutene starting materials, such as pentachlorobutanes.

In the chlorination of trans-1,4-dichlorobutene-2 by conventional processes, there is produced dl-isomer in appreciable quantities. Typically, the concentration of dl-isomer in the chlorination product is from about 25 to about 40%. Moreover, such chlorination processes also result in the production of undesirable higher chlorinated co-products or heavy ends, often produced in levels ranging from 5 to about 10% by weight. By contrast, in the chlorination process of this invention, at least about 90% of the trans-1,4-dichlorobutene-2 is converted to the meso-isomer. Likewise, the chlorination of 3,4-dichlorobutene-1 by the process of the instant invention results in a higher yield of the meso-isomer -- it is formed in proportions near the theoretical maximum, i.e., 50%. Also in the chlorination process of this invention, the formation of heavy ends is suppressed with the result that heavy ends are present in the reaction product mixture in concentrations of 2 wt.% or less. In a preferred embodiment of this invention wherein nitric oxide is additionally present during the chlorination reaction, the heavy ends formation is suppressed to levels considerably less than 1% by weight.

The feedstocks useful in practicing the instant invention are trans-1,4-dichlorobutene-2 and 3,4-dichlorobutene-1. These compounds are generally availble in mixtures containing other chlorinated compounds such as, for example, cis-1,4-dichlorobutene-2 and the trichlorobutenes. The presence of these materials is not deleterious to the process of the instant invention; however, concentrations of such compounds should be kept to a minimum inasmuch as they are chlorinated to products other than meso-1,2,3,4-tetrachlorobutane.

The preferred feedstock for practicing this invention is trans-1,4-dichlorobutene-2 since the tetrachloro product from the chlorination of this feedstock is substantially all meso-1,2,3,4-tetrachlorobutane. However, the chlorination of 3,4-dichlorobutene-1 also results in the production of meso-1,2,3,4-tetrachlorobutane; therefore, either trans-1,4-dichlorobutene-2, 3,4-dichlorobutene-1, or mixtures thereof are useful in practicing the instant invention.

The gist of the instant invention is that the manner in which the contacting of the dichlorobutenes and chlorine is effected is such that the chlorine concentration is maintained at as low a concentration as is practicable throughout the chlorination reaction period. High concentrations of chlorine are to be avoided since such high concentrations tend to promote the formation of dl-isomer and higher chlorinated derivatives, or heavy ends.

Since the reaction of chlorine with the olefinic materials present in the reaction zone is generally a relatively fast reaction, the relatively low chlorination rates which are the object of this invention are obtained by adjustment of the rate at which chlorine is introduced into the reaction zone. Generally, chlorine is introduced into the reaction zone at a rate of from about 0.01 to about 2.0 mole percent per minute based upon the amount of dichlorobutenes initially present. Preferably, the chlorine addition rate will be from about 0.1 to about 1.0 mole percent per minute, based upon the dichlorobutenes initially present.

The determination of an optimum chlorine addition rate within the aforementioned ranges will depend, in part, upon the manner in which the chlorine is introduced into the reaction zone. In one embodiment of this invention, chlorine is introduced into the liquid dichlorobutene reactants through a nozzle or plurality of nozzles extending into the liquid reactants. In an alternate embodiment, chlorine is introduced into the gas space above the liquid dichlorobutene reactants and the chlorination reaction takes place as the chlorine dissolves into the dichlorobutene reactants. In either embodiment, the addition of chlorine into the reaction zone is continued until the desired amount of the dichlorobutene starting materials have been chlorinated to products. Generally, the introduction of chlorine into the reaction zone in the gas space above the dichlorobutene reactants results in less production of heavy ends. Also, the lower the addition rate of chlorine into the reaction zone, the higher the proportion of meso-isomer produced and the lower the proportion of heavy ends produced.

In embodiments of this invention in which the chlorination is effected in a batch process, the chlorine addition rate ideally is a function of time. That is, as the dichlorobutenes are converted to tetrachlorobutane product, the chlorine addition rate is gradually reduced to maintain the desired low chlorination rate. Whenever the chlorination reaction has reached the point where a substantial proportion of the dichlorobutenes initially present have been converted to tetrachlorobutane products, the chlorine addition can be discontinued. However, it is equivalently useful to select an initial chlorine addition rate which results in a desirably low chlorination rate and to maintain this chlorine addition rate throughout the chlorination reaction period. Of course, it will be recognized that if a selected chlorine addition rate is maintained throughout the entire chlorination period, the concentration of chlorine in the reaction zone relative to the dichlorobutene reactants will increase as the dichlorobutenes are chlorinated. However, the advantage of the process of this invention is realized over substantially all of the reaction period except for the last small proportion of the dichlorobutenes to be chlorinated. Moreover, such a uniform chlorination rate additionally facilitates the maintenance of a uniform reaction zone temperature. Then, as that point of the chlorination reaction is reached at which substantially all of the dichlorobutenes have been reacted, there will result a sharp drop in the reaction zone temperature as the reaction exotherm decreases. At this point, the chlorine addition is terminated and the reaction zone is purged of residual chlorine. Of course, depending upon desired crude product specifications, the chlorine addition can be terminated prior to the chlorination of all of the dichlorobutenes present so as to avoid the high chlorine to dichlorobutene ratios. The unreacted dichlorobutenes can then be recovered and recycled to the reaction zone and be subsequently chlorinated to desired product.

In a continuous chlorination reaction process according to this invention, the relatively low chlorination rates are maintained by staged chlorine addition. That is, continuous addition of chlorine at a plurality of addition points located along the reaction zone. The chlorine addition rate at each of the plurality of chlorine addition locations can be the same or can decrease in rate in the downstream direction of the reaction zone as the dichlorobutene content of the reaction mixture decreases.

In the instant invention, chlorine can be introduced into the reaction zone as chlorine gas or as chlorine gas in admixture with a diluent gas which is inert to the reaction environment. Suitable diluent gases include the inert gases such as helium and argon; nitrogen; and saturated lower alkanes such as methane and ethane.

The total amount of chlorine required to effect the desired degree of chlorination in the process of this invention will depend upon the manner in which chlorine is introduced into the reaction zone. Stoichiometrically, one mole of chlorine is required for each mole of meso-1,2,3,4-tetrachlorobutane to be produced from the dichlorobutene starting materials. Generally, however, a slight excess of chlorine will be required to effect the desired degree of chlorination. In batch chlorinations wherein chlorine is introduced in admixture with an inert gas into the gas space of the reaction zone as hereinbefore described, a greater excess of chlorine will be required to effect a given level of chlorination than in the case of a batch chlorination wherein the chlorine alone is introduced directly into the liquid dichlorobutene reactant. However, the amount of excess chlorine required is generally not large and can, in any event, generally be recovered from the reaction zone and recycled for reuse.

In a preferred embodiment of the process of the instant invention, the chlorination reaction described herein is carried out in the additional presence of an effective amount of nitric oxide. By effective amount is meant that quantity of nitric oxide necessary to effectively suppress the formation of the undesirable dl-isomer and the higher chlorinated derivatives. Details as to the manner in which nitric oxide is employed in the process of this invention are to be found in my co-pending application, Ser. No. 484,575, of even date which is herein incorporated by reference.

It is desirable that there be provided in the reaction zone suitable means for agitating the liquid reaction mass to facilitate the contact of the chlorine or chlorine-containing gas with the dichlorobutenes. Agitation of the reaction mixture also insures that there is a good distribution of chlorine throughout the reaction mixture and that undesirably high chlorine concentrations are thereby avoided. Any number of agitator means are suitable, as will be apparent to one skilled in the art. For example, it has been found useful to employ propeller driven agitators, turbine blades, orifice mixing devices, inert gas spargers, and various baffle arrangements in the reaction zone.

The temperature at which the chlorination reaction of this invention is carried out is not critical and can vary over wide limits. It has been found that satisfactory results are obtained whenever the chlorination reaction as described herein is carried out at temperatures of from about 25°C. to about 150°C. A preferred temperature range for conducting the chlorination of trans-1,4-dichlorobutene-2 is from about 50°C. to about 100°C. Especially preferred are temperatures within these ranges above about 70°C., at which temperatures the meso-1,2,3,4-tetrachlorobutane product is liquid. Chlorinations carried out below about 65°C. result in a solid product being formed and thus requiring a reaction zone designed to accommodate slurry conditions.

The pressure at which the process of this invention is conducted is, likewise, not critical and can vary over rather wide limits. As a general proposition, the higher the reaction pressure selected, the higher the rate at which the chlorine is dissolved into the liquid reaction medium. Suitable reaction pressures can include subatmospheric pressure, atmospheric pressure or superatmospheric pressure. Generally, however, subatmospheric pressure is avoided because of the concomitant problems associated with the leakage of oxygen into the reaction system. Preferred reaction pressures are within the range of about 15 psia to about 100 psia, with reaction pressures of from about 15 psia to about 50 psia being especially preferred.

In carrying out the reaction according to the process of this invention, the reaction zone is initially purged of any contained oxygen. This purging action is generally commenced after the reaction zone has been charged with the liquid dichlorobutene reactants. The gas used for the purging operation is generally an inert gas such as helium and argon; nitrogen or a saturated hydrocarbon such as methane or ethane. The purging gas can additionally contain nitric oxide which acts as an oxygen scavenger. Generally, a purging gas of from about 2 to about 20 reactor volumes will be required in order to purge the reaction zone of the contained oxygen. Thereafter, chlorine is introduced into the reaction zone and the chlorination reaction is begun as herein described.

Although the process of the instant invention can be carried out in the absence of any solvent, it is equivalently useful to provide a solvent for the reactants. Suitable solvents generally include halogenated solvents such as methylene chloride, chloroform, carbon tetrachloride, and certain halogenated aromatic solvents such as chlorobenzene. Whenever a solvent is employed in the process of the instant invention, the amount is not critical and can vary. Solvent concentrations of from about 10 to about 90 wt.% are satisfactory, with concentrations of from about 25 to about 75 wt.% being preferred.

Subsequent to the reaction, the unreacted chlorine is generally removed from the crude product mixture and the desired meso-1,2,3,4-tetrachlorobutane product is thereafter recovered by conventional means, such as by fractional distillation, selective extraction, fractional crystallization and the like. Unreacted dichlorobutenes are recovered and recycled for further reaction according to the process of this invention. The meso-1,2,3,4-tetrachlorobutane is generally recovered in high purity from the crude product containing both the dl- and meso-isomers by conventional fractional crystallization techniques. The small proportion of trichloro compounds, generally present in the reaction mixture, may be recovered as a separate product.

As mentioned previously, meso-1,2,3,4-tetrachlorobutane is a compound of established utility. The meso-1,2,3,4-tetrachlorobutane is dehydrochlorinated to 2,3-dichlorobutadiene which is useful either alone or as a comonomer with chloroprene in the production of specialty rubber compositions.

To further illustrate the process of this invention, the following examples are provided. It should be understood that the details thereof are not regarded as limitations.

EXAMPLE I

This Example illustrates the effect of carrying out the chlorination of a feedstock consisting substantially of trans-1,4-dichlorobutene with smaller proportions of other dichlorobutenes at different chlorination rates. In each of the three runs, the feedstock was charged into a 5-liter, 3-necked flask equipped with a water jacket for cooling and an agitator means. After the dichlorobutene (DCB) feedstock was charged into the reactor flask, the system was then purged with a mixture of nitrogen containing about 10 mole percent nitric oxide. Thereafter, chlorine was introduced into the reaction mixture by means of a 4 mm nozzle extending down into the liquid dichlorobutene. The liquid reaction mixture was maintained under agitation throughout the chlorination period. The rate at which chlorine was introduced into the reaction flask was maintained at a rate which resulted in the indicated average chlorination rate. The temperature throughout the chlorination was maintained at 70°C. by adjusting the cooling water flow through the water jacket surrounding the reaction flask. The end of the chlorination reaction was determined to be that point at which the indicated temperature of the reaction flask contents began to decrease. The data for the three runs at different chlorination rates are presented in the following Table I.

TABLE I

| Run | A | B | C |
|---|---|---|---|
| Feed Composition, % | | | |
| 3,4-dichlorobutene-1 | 2.2 | 2.4 | 2.5 |
| cis-1,4-dichlorobutene-2 | 5.0 | 5.1 | 5.4 |
| trans-1,4-dichlorobutene-2 | 92.3 | 91.8 | 91.3 |
| Feed Charged, g. | 2966 | 2126 | 1022 |
| Chlorination Temp., °C. | 70 | 70 | 70 |
| Chlorination rate, | | | |
| Mol DCB chlorinated | | | |
| hr. | 4.0 | 2.8 | 0.8 |
| Product Composition, % | | | |
| Light ends (trichloro compounds) | 1.6 | 1.5 | 7.3 |
| dl-1,2,3,4-tetrachlorobutane | 26.9 | 15.9 | 10.3 |
| meso-1,2,3,4-tetrachlorobutane | 64.9 | 73.5 | 80.2 |
| Heavy ends (pentachlorobutanes) | 6.5 | 9.1 | 2.2 |

At the end of the reaction period, the product was worked up as follows. A heating medium was substituted for the cooling water in the water jacket and the temperature of the reaction flask contents was maintained at 70°C. The reaction flask was then purged with nitrogen to degas the system of the residual chlorine. Throughout the purging, the contents of the reaction flask were stirred to liberate any entrained chlorine. A sample from the reaction flask was dissolved in dichloromethane and analyzed by gas chromatographic techniques to yield the above analyses. The remaining contents of the reaction flask were then diluted with approximately one-half its volume of isopropyl alcohol. The mixture was then stirred rapidly and allowed to cool to 70°–75°F. At this temperature, crystallization of the meso-1,2,3,4-tetrachlorobutane was effected. The crystals after filtering and washing analyzed 99+ wt.% meso-1,2,3,4-tetrachlorobutane.

From the above data in Table I, it is apparent that reducing the chlorination rate from 4 to 0.8 mols per hour has a dramatic effect upon the isomer distribution of the tetrachlorobutanes produced, as well as on the proportion of heavy ends produced. The lower chlorination rates produce a product containing less of the dl-isomer and significantly less heavy ends. The meso-isomer is also maximized at the lower chlorination rate.

EXAMPLE II

In the following comparison, two chlorinations were effected at similar chlorination rates, but with differing modes of effecting contact of the chlorine with the dichlorobutenes to be chlorinated. In Run D, the chlorine was introduced into the liquid reaction medium through two 0.5 mm nozzles, whereas in Run E, the chlorine was introduced into the gas space above the liquid reaction medium and allowed to dissolve into the liquid wherein the chlorination took place. The procedure was otherwise the same as in Example I, except that in Run E the reaction flask was a one-liter flask inasmuch as the amount of dichlorobutenes being chlorinated was substantially smaller. The data from the two runs are presented in Table II.

TABLE II

| Run | D | E(b) |
|---|---|---|
| Feed Composition, % | | |
| 3,4-dichlorobutene-1 | 2.3 | 2.2 |
| cis-1,4-dichlorobutene-2 | 4.9 | 4.7 |
| trans-1,4-dichlorobutene-2 | 92.1 | 92.6 |
| Feed Charged, g. | 2978 | 307 |
| Chlorination Temp.°C. | 70 | 70 |
| Chlorination rate, | | |
| Mol DCB chlorinated | | |
| hr. | 1.7(a) | 1.5(c) |
| Product Composition, % | | |
| Light ends (trichloro compounds) | 5.3 | 6.5 |
| dl-1,2,3,4-tetrachlorobutane | 8.3 | 6.9 |
| meso-1,2,3,4-tetrachlorobutane | 82.5 | 84.9 |
| Heavy ends (pentachlorobutanes) | 3.8 | 1.6 |

(a)Approximately 380–450 cc/min chlorine through each of two 0.5 mm nozzles for total of 14 hours.
(b)1-liter reaction flask.
(c)Chlorine introduced into gas space above liquid reactants for total of 1.67 hours.

EXAMPLE III

The following Example illustrates another embodiment of the process of this invention in which the contact between the chlorine and the dichlorobutene is effected by introducing the chlorine into the reaction zone through a nozzle which discharges directly into the liquid dichlorobutene reactants. In Run C, the chlorine is introduced into the reaction mixture through a 4 mm. nozzle. In Run F, the chlorine is introduced into the reaction mixture through a 0.5 mm. nozzle at a relatively higher gas velocity. The data from the two runs is presented in Table III.

TABLE III

| Run | C | F |
|---|---|---|
| Feed Composition, % | | |
| 3,4-dichlorobutene-1 | 2.5 | 2.2 |
| cis-1,4-dichlorobutene-2 | 5.4 | 4.7 |
| trans-1,4-dichlorobutene-2 | 91.3 | 92.6 |
| Feed Charged, g. | 1022 | 436 |
| Chlorination Temp.,°C. | 70 | 70 |
| Chlorination rate, | | |
| Mol DCB chlorinated | | |
| hr. | 0.8 | 0.95* |
| Product Composition, % | | |
| Light ends (trichloro compounds) | 7.3 | 7.5 |
| dl-1,2,3,4-tetrachlorobutane | 10.3 | 6.4 |
| meso-1,2,3,4-tetrachlorobutane | 80.2 | 84.4 |
| Heavy ends (pentachlorobutanes) | 2.2 | 1.6 |

*Approximately 400 cc/min chlorine for a total of 3.67 hours.

From the above data, it is apparent that even at the slightly higher chlorination rate, the effect of the smaller nozzle size and correspondingly better gas mixing results in an even lower heavy ends production and a better meso-isomer distribution.

EXAMPLE IV

The following example illustrates a preferred embodiment of this invention in which the chlorine was introduced into the reaction zone in the gas space above the liquid reactants. In Run F, the chlorine was introduced into the liquid reaction medium through a 0.5 mm. nozzle, wherein in Run E, the chlorine was introduced into the reaction zone in the gas space above the liquid reactants. The data from the two runs are presented in Table IV.

TABLE IV

| Run | F | E |
|---|---|---|
| Feed Composition | | |
| 3,4-dichlorobutene-1 | 2.2 | 2.2 |
| cis-1,4-dichlorobutene-2 | 4.7 | 4.7 |
| trans-1,4-dichlorobutene-2 | 92.6 | 92.6 |
| Feed Charged, g. | 436 | 307 |
| Chlorination Temp.,°C. | 70 | 70 |
| Chlorination rate, | | |
| Mol DCB chlorinated | | |
| hr. | 0.95* | 1.5** |
| Product Composition | | |
| Light ends (trichloro compounds) | 7.5 | 6.5 |
| dl-1,2,3,4-tetrachlorobutane | 6.4 | 6.9 |
| meso-1,2,3,4-tetrachlorobutane | 84.4 | 84.9 |
| Heavy ends (pentachlorobutanes) | 1.6 | 1.6 |

* Approximately 400 cc/min chlorine for a total of 3.67 hours.
**Chlorine introduced into gas space above liquid reactants for a total of 1.67 hours.

From the above, it is apparent that the chlorination rate was increased by over 50% without adversely affecting the meso-isomer yield or the heavy ends yield when introducing the chlorine into the reaction flask in the gas space above the liquid dichlorobutenes and allowing the contact to come about as the chlorine dissolved into the liquid phase where the chlorination reaction was effected.

From the foregoing description and Examples of this invention, those of ordinary skill in the art may make many modifications and variations therefrom without departing from the scope of the invention as hereinafter claimed.

I claim:

1. In a process for the production of meso-1,2,3,4-tetrachlorobutane by contacting in a reaction zone trans-1,4-dichlorobutene-2 in the liquid phase with chlorine in the substantial absence of oxygen the improvement which comprises:

effecting said contacting at a temperature in the range of from about 50° to 100° C. in the absence of a catalyst by introducing the chlorine into the reaction zone containing the trans-1,4-dichlorobutene-2 at a rate of from about 0.01 to about 2.0 mole percent per minute based on the amount of trans-1,4-dichlorobutene-2 initially present, for a period of time sufficient to effect the desired chlorination of the trans-1,4-dichlorobutene-2.

2. The process according to claim 1 wherein said contacting is effected by introducing the chlorine into the gas space of the reaction zone containing the liquid trans-1,4-dichlorobutene-2.

3. The process according to claim 1 wherein said contacting is effected by introducing the chlorine into the liquid trans-1,4-dichlorobutene-2-containing reaction mixture.

4. The process according to claim 1 wherein said contacting is effected in a continuous flow reaction zone wherein the chlorine is introduced into the reaction zone at a plurality of points along the reaction zone.

5. In a process for the production of meso-1,2,3,4-tetrachlorobutane by contacting in a reaction zone trans-1,4-dichlorobutene-2 in the liquid phase with chlorine at a temperature of from about 25° C. to about 150° C. in the substantial absence of oxygen the improvement which comprises:

effecting said contacting by introducing the chlorine into the reaction zone containing the trans-1,4-dichlorobutene-2 at a rate of from about 0.01 to about 2.0 mole percent per minute based on the amount of trans-1,4-dichlorobutene-2 initially present, for a period of time sufficient to effect the desired chlorination of the trans-1,4-dichlorobutene-2 wherein said contacting is carried out in the additional presence of an effective amount of nitric oxide for suppressing the formation of the dl-1,2,3,4-tetrachlorobutane and the more highly chlorinated derivatives of the tetrachlorobutanes.

6. The process according to claim 5 wherein the chlorine is introduced into the reaction zone at a rate of from about 0.1 to about 1 mole percent per minute based on the amount of trans-1,4-dichlorobutene-2 initially present.

7. The process according to claim 5 wherein said contacting is effected by introducing the chlorine into the gas space of the reaction zone containing the liquid trans-1,4-dichlorobutene-2.

8. The process according to claim 5 wherein said contacting is effected by introducing the chlorine into the liquid trans-1,4-dichlorobutene-2 containing reaction mixture.

9. The process according to claim 5 wherein said contacting is effected in a continuous flow reaction zone wherein the chlorine is introduced into the reaction zone at a plurality of points along the reaction zone.

10. The process according to claim 1 wherein the temperature is above about 70° C.

11. A process for the production of meso-1,2,3,4-tetrachlorobutane comprising:

contacting trans-1,4-chlorobutene-2 in the liquid phase with chlorine at a temperature in the range of from about 50° to 100° C. in the substantial absence of oxygen and in the absence of catalysts, introducing said chlorine at a rate of from about 0.01 to about 2.0 mole percent per minute based on the amount of trans-1,4-dichlorobutene-2 initially present and recovering meso-1,2,3,4-tetrachlorobutane.

* * * * *